United States Patent [19]
Davidson

[11] Patent Number: 4,735,625
[45] Date of Patent: Apr. 5, 1988

[54] BONE CEMENT REINFORCEMENT AND METHOD

[75] Inventor: James A. Davidson, Germantown, Tenn.

[73] Assignee: Richards Medical Company, Memphis, Tenn.

[21] Appl. No.: 775,012

[22] Filed: Sep. 11, 1985

[51] Int. Cl.⁴ ................... A61F 2/28; A61F 2/30; A61F 2/32

[52] U.S. Cl. ..................... 623/16; 623/22; 623/23

[58] Field of Search ............... 623/16, 22, 23; 128/92, 128/92 W; 428/902; 526/348.1

[56] References Cited

U.S. PATENT DOCUMENTS

| | | | |
|---|---|---|---|
| 3,924,274 | 12/1975 | Heimke et al. | 623/18 |
| 4,064,567 | 12/1977 | Burstein et al. | 623/22 |
| 4,164,794 | 8/1979 | Spector et al. | 623/22 X |
| 4,222,128 | 9/1980 | Tomonaga et al. | 623/16 |
| 4,283,799 | 8/1981 | Pratt, Jr. et al. | 623/23 |
| 4,413,110 | 11/1983 | Kavesh et al. | 526/348.1 |

Primary Examiner—Richard J. Apley
Assistant Examiner—Alan W. Cannon
Attorney, Agent, or Firm—Pravel, Gambrell, Hewitt, Kimball & Krieger

[57] ABSTRACT

A reinforcing technique for bone cement used in the anchoring of prosthetic devices. The reinforced bone cement includes oriented reinforcement formed of a continuous fiber-like material that is embedded in the bone cement between at least a portion of the outer surface of the prosthetic device and the surrounding bone that defines the cavity in which the device is implanted. The reinforcement is preferably a polymeric mat embedded in a thin layer of bone cement forming a precoat on the outer surface of the implant.

14 Claims, 3 Drawing Sheets

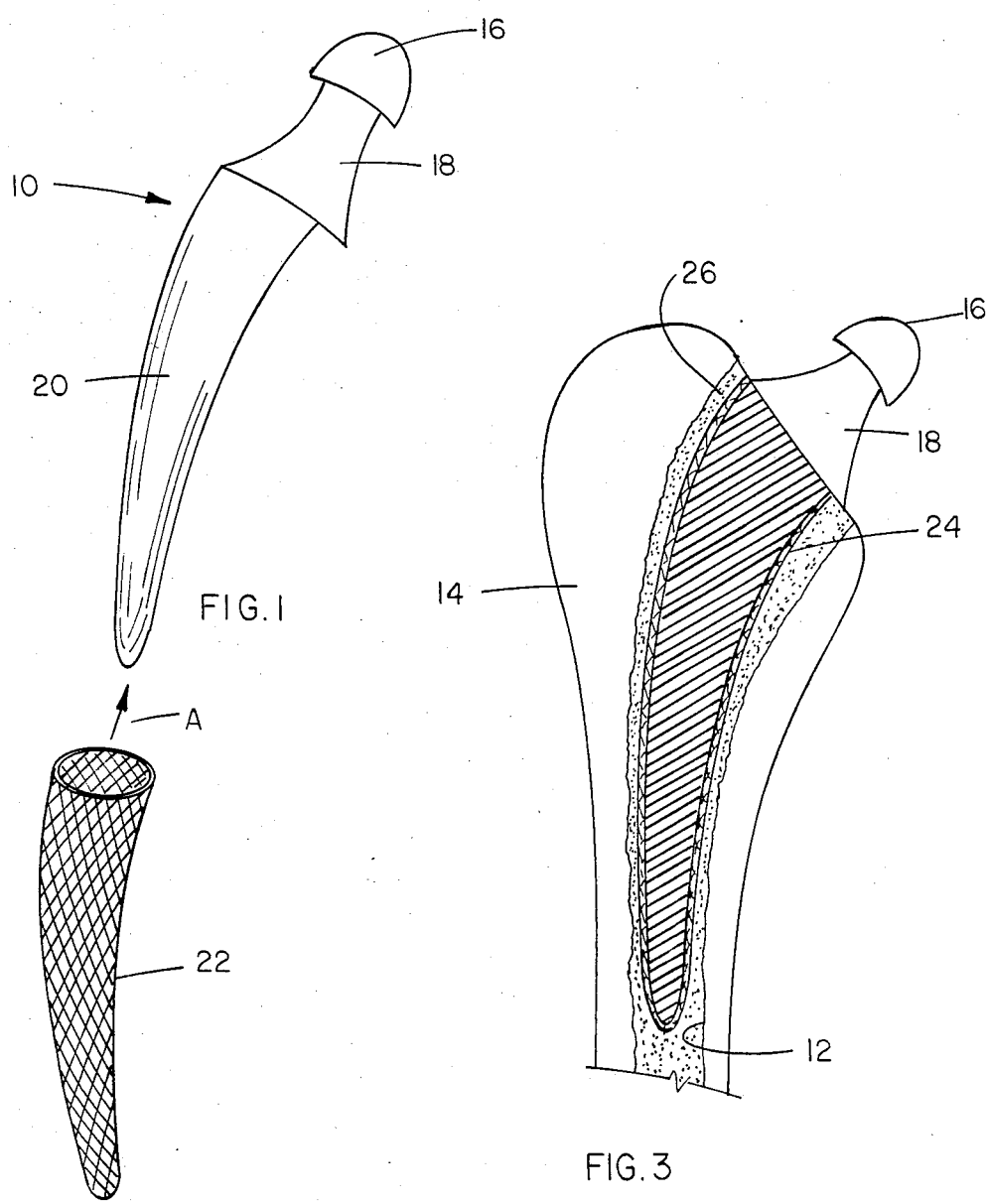

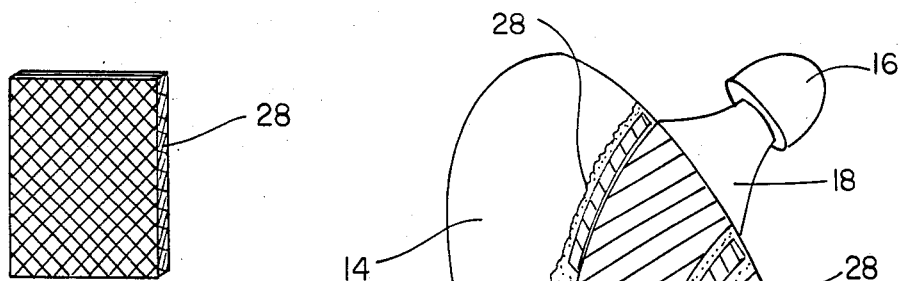
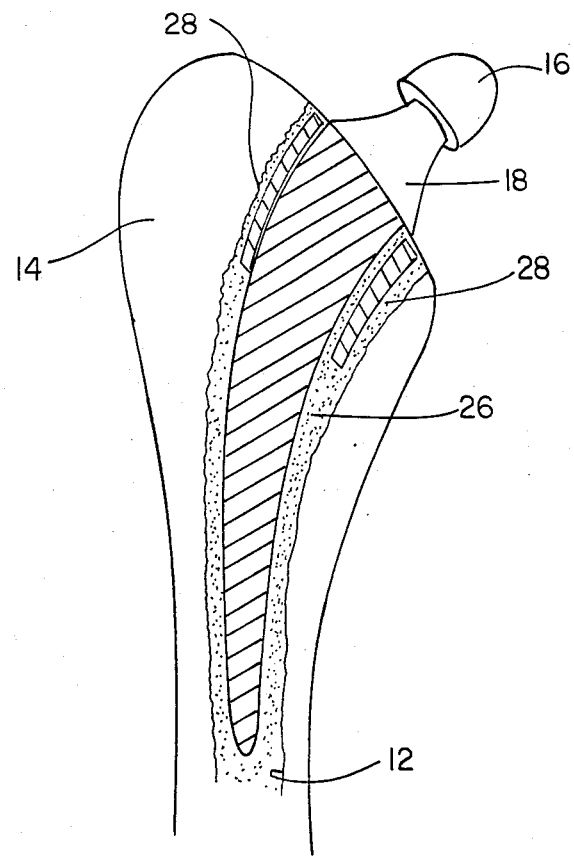
FIG. 4
FIG. 6
FIG. 5
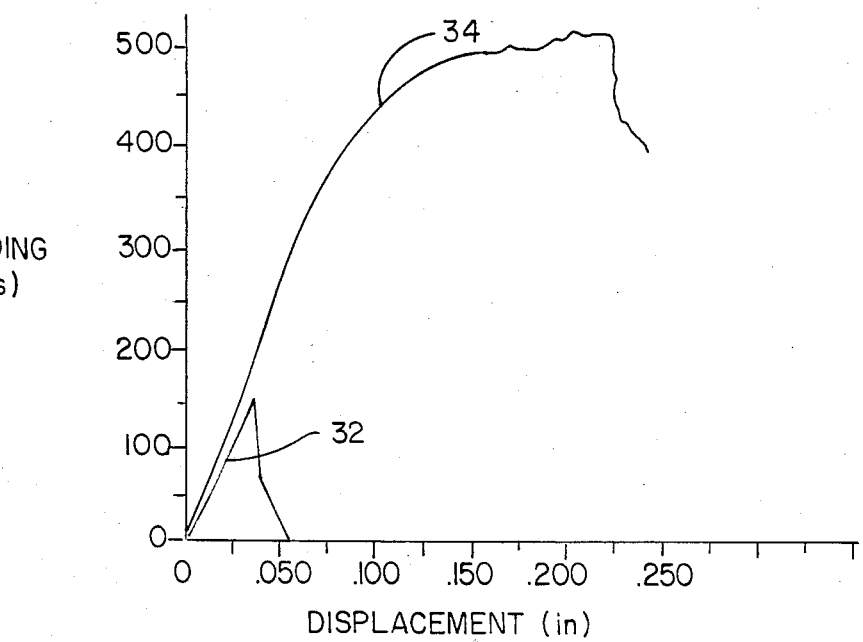
FIG. 7

BONE CEMENT REINFORCEMENT AND METHOD

FIELD OF THE INVENTION

The present invention relates to prosthetic devices that are anchored in bone cavities through the use of bone cement and, more particularly, to a reinforcement for cemented prostheses that operates to increase both the fatigue and static fracture resistance of bone cement.

BACKGROUND OF THE INVENTION

Prosthetic human body implants can be anchored in bone through a variety of different techniques such as friction fit, threads, porous areas for tissue ingrowth and bone cements. The use of a bone cement such as polymethyl methacrylate (PMMA) is the most popular technique for implant fixation even though when cured most cements have a substantially lower strength than that of cortical bone. When the strength of cement are exceeded, the cement tends to crack and cause the prosthetic device to become loosened.

These strength limitations are especially troublesome for the femoral stem portion of a hip prosthesis where tensile strains of 1000 microstrain can routinely occur. Cyclic strains of this magnitude can tend to break down a typical PMMA fixated stem due to fatigue cracking during as little as 1,000,000 repetitions, which can typically occur in a year's time. Moreover, a single loading of event that creates a tensile load in excess of about 9,000 pounds per square inch has been found to fracture PMMA. Stress studies indicate that the fatigue limits of PMMA bone cement can be exceeded in normal daily activities, such as walking or climbing stairs. Moreover, sudden impacts such as a fall can greatly exceed the tensile limits of PMMA bone cement and shatter or fracture the cement instantaneously.

PMMA bone cement has a compressive strength that is 50-70% of that of cortical bone; one-tenth the modulus of elasticity; one-fourth the tensile strength; 60% of the shear strength; and less than one-half the fatigue strength. These limitations have for years restricted the use of cemented prosthetic devices to patients that would not be particularly active after receiving such an implant.

Attempts have been made to increase the static and fatigue integrity of bone cement that include the addition of randomly oriented fibers formed of materials such as Kevlar, carbon, metal and other fibers. The use of such fibers has not proven satisfactory because intrusion properties of the bone cement are adversely affected and the fibers tend to shed and migrate throughout the body.

Other techniques such as ultrasonic and vacuum mixing, changing the powder to liquid ratio and centrifugation have also been used. The latter technique has generally been regarded as providing the most important improvement in PMMA bone cement over the past 25 years since it tends to reduce cement porosity.

A precoat of bone cement to the prostheses has also been proposed and although it does improve substrate-cement interface strength between the prosthesis and cement, the precoat does not improve static, fatigue and impact resistance.

As a result of these difficulties in developing a prosthesis for active patients that can be anchored through the use of bone cement, other techniques are actively being pursued at the present time. These include various surface configurations for providing a better mechanical fit between the prosthesis and cavity and porous coatings that promote tissue ingrowth. However, these proposed solutions are presently undergoing development and have not resulted in an implant that is universally acceptable for all applications. Although the use of ingrowth promoting surfaces is generally regarded as having great promise, these types of devices tend to be significantly more expensive than those that are designed to be anchored through the use of bone cement and require a longer recovery time before the patient can become active.

SUMMARY OF THE INVENTION

The present invention is directed to a reinforcing technique for bone cement that significantly increases both the fatigue and static fracture resistance of bone cement. The reinforcing technique includes the use of an oriented reinforcement formed of a continuous fiber-like material that is embedded in the bone cement between at least a portion of the outer surface of the prosthetic device and the surrounding bone that defines the cavity in which the device is implanted. The reinforcement can be formed of a plurality of such as polymeric metallic ceramic or carbon, in single or multiple form, oriented in at least one direction for optimization of the properties of bone cement.

The reinforcement can be used in the form of a precoat to the prosthetic device where the reinforcement is embedded in a thin layer of bone cement applied to the outer surface of the implant. A second layer of bone cement can then be applied to the outer surface of the implant and worked into the fibers to form a composite coating. The precoat is then allowed to cure. Alternatively, the precoat can be formed without first applying bone cement to the prosthesis or even by coating the reinforcement material with bone cement prior to applying the reinforcement to the device. Additional bone cement can be applied to the outer surface to provide a smooth appearance.

When the precoated implant is inserted in uncured bone cement already in the cavity, a chemical bond forms between the bone cement in the cavity and the bone cement used to form the precoat, while there are mechanical bonds between the bone cement and the implant and surrounding bone. Alternatively, a material such as hydroxylapatite can be applied to the outer surface of the precoat for providing a surface to which adjacent bone will become biologically attached. A prosthesis so prepared can be press fitted in the cavity and fixed without the need for additional bone cement.

The reinforcement can be placed over the entire portion of the implant that is to be affixed within the bone cavity or some portion of the outer surface, preferably where stress concentrations are greater. It has been found that a reinforcement in the form of a mantle or sock in which the stem portion of a hip prostheses can be inserted provides an easy configuration for applying the reinforcement to a prosthesis.

Alternately, or in addition to the use of the precoat discussed above, a reinforcement can be interposed in the bone cement between the outer surface of the prosthetic device and the surrounding bone that forms the cavity in which the device is to be implanted. Such a reinforcement can advantageously be placed at some point between the two surfaces and provide the reinforcing characteristics in accordance with the invention.

The reinforcement preferably is formed of a plurality of biocompatible fibers of a polymeric material that have a weight average molecular weight at least about 500,000.

The preferred material is known as high-strength polyethylene that has a weight average molecular weight at least about 500,000. The preferred material also has a tenacity of at least about 20 g/denier, a tensile modulus at least about 500 g/denier, a creep value no more than about 5% (when measured at 10% of breaking load for 50 days at 23° C.), a porosity less than about 10% and a main melting temperature of at least 147° C. (measured to 10° C./min. heating rate by differential scanning calorimetry). Fibers formed of other polymeric materials such as polypropylene or blends of several types of fibers are also believed to be useful. Such fibers and methods for fabricating them are disclosed in U.S. Pat. No. 4,413,110 to Kavesh et al, which is incorporated by reference herein as though fully set forth. The preferred material made in accordance with the foregoing patent is a material sold by Allied Corporation under the name A-900 or A-1000 high strength polyethylene fiber. However, fiber formed of other biocompatible materials such as carbon, titanium and Type 316 Stainless Steel can be used.

The reinforcement is formed by a plurality of such fibers oriented in at least one general direction and interconnected to form a network. Preferably, the reinforcement is formed in the shape of a mantle or sock with the fibers formed into threads that are interwoven in two or more general directions for forming a flexible sleeve that can easily be slipped over the stem of a prosthetic device that has already been coated with a thin film of bone cement. Another thin coat of cement is applied to the outer surface of the reinforcement and worked into the oriented fibers. The second layer is smoothed and allowed to dry, the total thickness of the composite being about 1-2 mm. The precoated stem is then inserted into a bone cavity in which bone cement is already been placed, a chemical bond forming between the bone cement and the cavity and that used as part of the precoat.

The use of such a reinforcement has been found to increase the impact resistance of bone cement, its resistance to catastrophic cracks and torsional and flexural fatigue. This technique is believed to allow cemented prostheses to be implanted in younger more active patients and effectively remain in place for longer periods of time. Prostheses formed in accordance with the invention will be less costly than ones being developed to accommodate tissue ingrowth through the use of porous coatings.

The prosthetic device with the composite precoat could also be fixed in bone through the use of a press fit instead of being embedded in cement applied to the body cavity. When fixed by using this technique, the precoat can further include particles of hydroxylapatite (HA) impregnated in the precoat surface to promote the growth of bone tissue up to the HA/composite surface.

BRIEF DESCRIPTION OF THE DRAWINGS

A better understanding of the invention can be obtained when the detailed description of exemplary embodiments set forth below is considered in conjunction with the appended drawings, in which:

FIG. 1 is a perspective view of a typical hip prosthesis;

FIG. 2 is a perspective view of a fibrous mantle sized and shaped to fit over the stem portion of the hip prosthesis of FIG. 1;

FIG. 3 is a sectional view of the hip prosthesis of FIG. 1 with a composite coating on it including the mantle of FIG. 2, after being implanted in the intermedullary canal of a femur;

FIG. 4 is a reinforcement section formed in accordance with the invention;

FIG. 5 is a sectional view that illustrates the placement of reinforcement such as those shown in FIG. 4 in bone cement between the orthopedic implant and cavity wall of an intermedullary canal similar to that of FIG. 3;

FIG. 6 is a perspective view of an alternative embodiment of the mantle of FIG. 2;

FIG. 7 is a graph showing the comparative results of bend tests of PMMA bone cement versus surface reinforced bone cement in accordance with the present invention.

DETAILED DESCRIPTION OF EXEMPLARY EMBODIMENTS

Figure 8:
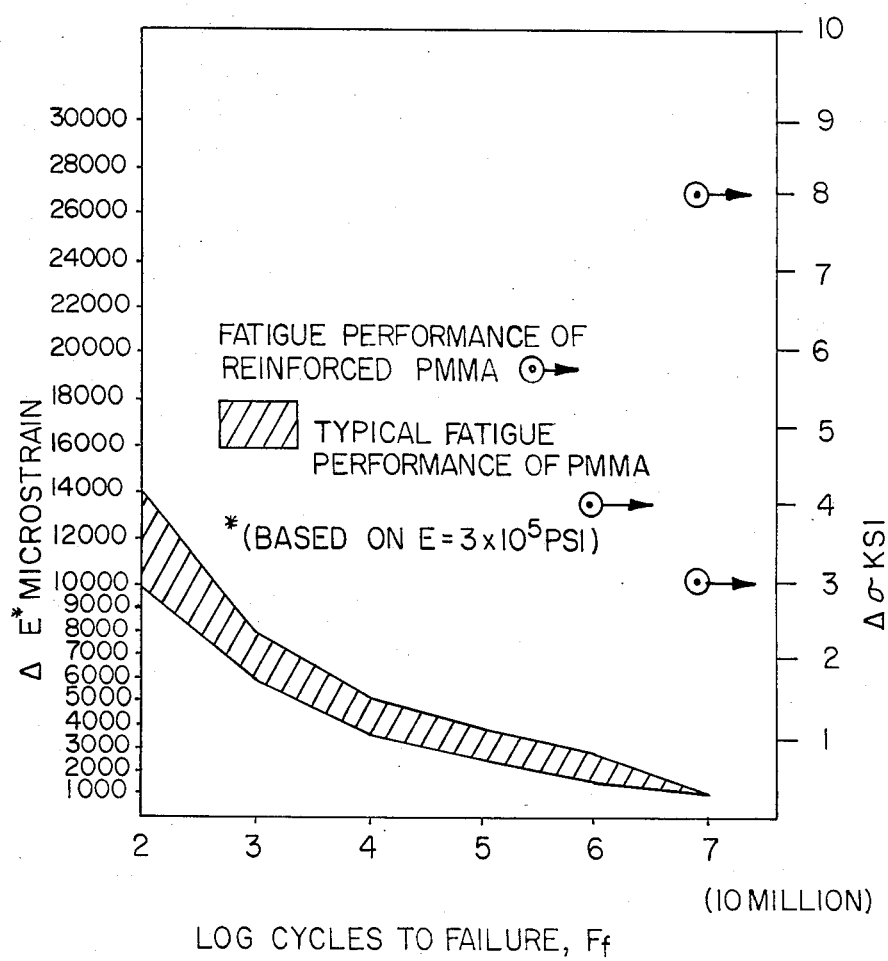
FIG. 8 is a graph showing the comparative results of fatigue behavior of PMMA bone cement versus reinforced bone cement in accordance with the present invention.

Referring to the drawings, the invention is described in conjunction with a hip joint prosthesis 10 designed to be anchored in place in a reamed-out intermedullary canal 12 of a femur 14 (See FIG. 3). The prosthetic device 10 includes a head 16 adapted to fit within the acetabular cup portion of the prosthetic device (not shown) that is inserted in the pelvis (not shown) of the patient. The head 16 is connected through a neck 18 to a stem 20 that is the portion of the prosthesis 10 inserted in the intermedullary canal 12.

As shown in FIG. 2, a reinforeement 22 in the shape of a mantle or sock formed of a plurality of fibers of a polymeric material is sized and shaped to fit over a substantial portion of the stem 20 as shown in FIG. 3 and illustrated by arrow A. The reinforcement 22 is formed of fibers that are oriented in two general directions and interconnected to form a flexible network that can easily fit over the stem 20. The fibers are preferably formed of high-strength polyethylene sold by Allied Corporation under the name A-900 or A-1000 high strength fiber polyethylene fiber. Other polymeric materials with a weight average molecular weight at least about 500,000, such as those described in U.S. Pat. No. 4,413,110 described above could also be used.

In one embodiment of the invention, the reinforcement 22 is used to form part of a composite precoat for the stem 20 before it is inserted into the intermedullary canal 12. This precoat is formed by first coating the stem 20 with a thin film of bone cement such as PMMA and then placing the reinforcement 22 over the bone cement before it completely dries. Additional bone cement is applied to the outer surface of the reinforcement 22 and worked into the fibers and original layer of cement until the precoat is smooth, so that the total composite coating thickness is about 1-2 millimeters. The precoat is then allowed to cure and then trimmed or finished as desired. It can be appreciated that this process encapsulates reinforcement 22 within the bone cement.

The precoat is generally designated by reference numeral 24 in FIG. 3, where the prosthesis 10 is shown as being implanted in the femur 14. Implantation takes place by first cutting off the upper portion of the femur 14 (not shown) and then reaming a hole or cavity in the intermedullary canal 12. After the cavity is appropriately sized and shaped, a quantity of bone cement 26 is prepared and inserted into the cavity. The stem 20 is inserted into the bone cement and the prosthesis is placed so that the neck 18 and head 16 are oriented at the proper angle relative to the femur 14 and acetabulum cup (not shown). As the cement 26 cures, it forms a chemical bond with the cement portion of the precoat 24 and firmly anchors the hip prosthesis 10 in the intermedullary canal.

Instead of anchoring the prosthesis 10 of FIG. 3 to the femur 14 through the bone cement 26, the composite coating described above can be coated with a layer of material such as hydroxylapatite (not shown) or other suitable material that can become biologically attached to adjacent bone by promoting bone tissue attachment. The prosthesis coated in this manner is press-fitted into an appropriately sized cavity. Adjacent bone and other tissue will then grow up to the irregularities in the outer surface of the hydroxylapatite coatings and anchor the prosthesis in place As shown in FIGS. 4 and 5, a mat 28 that is generally rectangular in shape formed of polymeric fibers oriented in two general directions can be interposed in the bone cement 26 between the outer surface of the stem 20 and the bone wall 14 that defines the cavity in which the stem is to be inserted. These mat sections 28 can be embedded in the bone cement 26 prior to insertion of the stem 20 in the bone cavity.

As shown in FIG. 5, the mat sections 28 are preferably located in the upper portions of the stem 20 where the peak loads occur when the patient is walking or otherwise moving around. The mat sections 28 could be in the shape of a general cylindrical mantle similar to that of FIG. 2 and embedded in the bone cement 26 without being part of a composite precoat of the type shown in FIG. 3 or be used at the same time and in addition to the precoat of FIG. 3.

A reinforcement can also be formed as shown in FIG. 6 where a mantle or sock section 30 is shown where the polymeric fibers used to form the mantle 30 are oriented in one general direction as opposed to two general directions described in conjunction with the embodiments of FIGS. 2 and 4. It is important that the fibers be oriented in at least one general direction and wrapped around the prosthesis or preformed into a shaped section where the individual fibers are oriented, as opposed to being randomly dispersed throughout the bone cement. The oriented fiber reinforcement resists loading of the prosthesis 10 and prevents the fibers from migrating out of the bone cement into other portions of the human body as has been found in the past.

FIG. 7 is a graph that shows the comparative test results of specimens formed of PMMA with and without being reinforced with a mat of polymeric fibers made in accordance with the invention. Specimens were prepared of PMMA bone cement that were 0.29 inches thick and 0.50 inches wide and greater than 1.5 inches long. Other specimens were formed using PMMA bone cement of the same dimensions wherein a fibrous mat formed of polymeric fibers of the type sold by Allied Corporation under the name A-900 high strength polyethylene fiber having 400,000 psi tensile strength were cemented onto one surface of the samples through the use of PMMA, forming a layer of fabric along the top surface of the specimens. The mat was woven into a two-directional network at 30° and 60° relative to longitudinal stress axis of the specimen.

The specimens were subjected to three-point bending with force supplied to the tops of the specimens at a point 1.5 inches apart with a static bending surface on which the specimens rested midway between the two upper force application points. During the test the specimens were placed in tension by the application of downward force and the specimen loaded to maximum load. The graph of FIG. 7 shows representative results of these tests. This graph represents the displacement in inches versus loading in pounds with reference numeral 32 being used to identify the results of the tests on the PMMA specimen and reference numeral 34 the results of the specimens reinforced as described.

As shown, the pure PMMA bone cement specimen failed in a brittle manner at a maximum load of about 153 pounds. The fracture energy (e.g., area under the curve to maximum load) reflects the brittle nature of pure PMMA bone cement. The composite of the PMMA bone cement and UHMW polyethylene mantle illustrates a peak load of 525 pounds, a level 3.4 times greater than PMMA bone cement that was not reinforced. Further, the composite specimen did not fail in a brittle manner as reflected by its exceptional fracture energy (e.g., area under curve 34). This energy level is 32 times greater than that for the non-reinforced PMMA bone cement specimen.

The fatigue behavior of PMMA bone cement and the reinforced PMMA bone cement of the present invention are compared in FIG. 8. Specimens similar to those prepared for the test described above in conjunction with FIG. 7 were used to evaluate fatigue behavior. The specimens were tested cyclically at a frequency of 5 hz. in a 3 point loading fixture. The ratio of the minimum cyclic load divided by the maximum cyclic load was 0.1 (tension-tension bending). The graph of FIG. 8 represents the $\Delta E$, microstrain based upon $E = 3 \times 10^5$ psi versus log cycles to failure. The graph results show that an improvement in fatigue performance of the reinforced sample over the that of unreinforced PMMA bone cement. The specimens tested at $\Delta \sigma = 8$ psi developed a small surface crack after a few hundred cycles but were able to continue to support the load for more than 10,000,000 additional cycles. As shown by the shaded area, unreinforced PMMA bone cement is only capable of sustaining a cyclic stress of 0.4 psi for 10,000,000 cycles.

For the reinforced PMMA bone specimen, it was observed that small cracks that did develop during testing were arrested at the fiber reinforcement with no fragmentation. The combination of exceptionally high fracture energy and bending strength of the composite specimen is believed to allow for periodic high load events without catastrophic failure of a prosthetic device, which are typically encountered with cemented implant devices.

It should be understood that the foregoing description and drawings of the invention are not intended to be limiting but are exemplary of the invention and that improvements and modifications will be made to the invention that still fall in the scope of the appended claims.

I claim:

1. A prosthetic device with a reinforced composite precoat, comprising:
   a. a prosthetic device adapted to have at least a portion implanted in a cavity formed in animal bone;
   b. a relatively thin layer of cured bone cement precoated on the outer surface of the prosthetic device before implantation on at least part of the portion adapted to be implanted in the bone cavity; and
   c. a reinforcing fibrous mat formed of high strength polyolefin fibers encapsulated within the cured bone cement precoating so that the fibers define a reinforcement to the cured bone cement layer prior to implantation, the fibers being oriented in at least one direction and interconnected to form a flexible network; and
   d. the precoating outer layer defining a cured bone cement surface covering the fibers to provide a generally smooth outer layer so that the cured bone cement surface can be used to cary wet cement for forming a bond between the precoat and the animal bone.

2. The invention of claim 1, wherein the layer of bone cement is about 1–2 mm thick.

3. The invention of claim 1, wherein the fibers are formed of polyethylene, having a weight average molecular weight at least about 500,000, with a tenacity of at least about 20 g/denier, a tensile modulus at least about 500 g/denier, a creep value no more than about 5% (when measured at 10% of breaking load for 50 days at 23° C.), a porosity less than about 10% and a main melting temperature of at least 147° C. (measured to 10° C./min. heating rate by differential scanning calorimetry).

4. The invention of claim 1 wherein the fibers are formed of polyethylene being of a weight average molecular weight of at least about 1,000,000 and having a tensile modulus of at least about 1600 g/denier, a main melting temperature of at least about 147° C. (measured at 10° C./minute heating rate by differential scanning calorimetry) and an elongation-to-break of not more than 5%.

5. The invention of claim 1 wherein the fibers are formed of polypropylene being of a weight average molecular weight of at least about 750,000 and having a tenacity of at least about 8 g/denier, a tensile modulus of at least about 160 g/denier and a main melting temperature of at least about 168° C. (measured at 10° C./minute heating rate by differential scanning calorimetry).

6. The invention of claim 1 wherein the mat is formed of a blend of polyethylene and polypropylene fibers.

7. The invention of claim 1 wherein the fibers are formed into threads that are oriented in two general directions and woven together.

8. The invention of claim 1 wherein the mat is formed as a sock that is sized and shaped to fit over an elongated portion of a prosthesis.

9. The invention of claim 1 wherein the mat is formed rectilinear in shape.

10. The invention of claim 1, wherein the mat is impregnated with the bone cement.

11. The invention of claim 1, wherein the mat is bonded to the prosthetic device by first applying a first layer of bone cement to the device, placing the mat on the cement, and applying sufficient bone cement to the mat to bond with the first layer of cement through the fibers.

12. The invention of claim 1, wherein the mat is formed as a sock that is sized and shapted to fit over an elongated portion of the prosthesis.

13. The device of claim 1, further including a coating of a material on the outer surface of the precoat that is capable of becoming biologically attached to surrounding bone.

14. The device of claim 13, wherein the coating is formed of hydroxylapatite.

* * * * *